United States Patent [19]

Ueyama et al.

[11] Patent Number: 5,075,453

[45] Date of Patent: Dec. 24, 1991

[54] PROCESS FOR PRODUCING ARYLOXY-SUBSTITUTED PHOSPHAZENE DERIVATIVES

[75] Inventors: Shinichiro Ueyama, Tokyo; Kazuhiko Fujikawa, Kounosu; Yasuhiro Yoshikawa, Sagamihara; Tetsuhiko Okamoto, Tokyo; Masayuki Furukawa, Saitama; Tadaichi Nishikawa, Kamakura, all of Japan

[73] Assignee: Nippon Soda Co., Ltd., Tokyo, Japan

[21] Appl. No.: 401,570

[22] Filed: Aug. 29, 1989

Related U.S. Application Data

[63] Continuation of Ser. No. 157,321, Feb. 18, 1988, abandoned.

[30] Foreign Application Priority Data

Feb. 18, 1987 [JP] Japan ................. 62-033423
May 27, 1987 [JP] Japan ................. 62-127993
May 29, 1987 [JP] Japan ................. 62-131849

[51] Int. Cl.$^5$ .......................... C07D 207/40
[52] U.S. Cl. ....................... 548/413; 558/80
[58] Field of Search ............... 558/80; 544/11, 157; 546/22; 548/413

[56] References Cited

U.S. PATENT DOCUMENTS 4,305,891 12/1981 Jones ..................... 558/98
4,550,177 10/1985 Kumar et al. ............ 548/413
4,600,791 7/1986 Carr et al. ............... 558/80
4,748,263 3/1988 Kumar et al. ............ 558/80

FOREIGN PATENT DOCUMENTS 0091367 10/1983 European Pat. Off. .

OTHER PUBLICATIONS

J. Polymer Science: "High-Strength Fire-and Heat-Resistant Inide Resins Containing Cyclotriphosphazene and Hexafluroisopropylidene Groups", vol. 11, 927-943 (1984).

Allcock, H. R.: Phosphorous—Nitrogen Compounds; Academic Press Inc., (1972); pp. 150-155.

Feiser & Feiser *Reagents for Organic Synthesis* vol. 4 p. 416.

*Primary Examiner*—Robert W. Ramsuer
*Assistant Examiner*—Jacqueline Haley
*Attorney, Agent, or Firm*—Lowe, Price, LeBlanc & Becker

[57] ABSTRACT

A process for producing an aryloxy-substituted phosphazene derivative represented by the formula $$(N=P)_n(OAr)_l Cl_{m-l} R^1_p \quad \text{(III)}$$

which comprises reacting a chlorophosphazene derivative represented by the general formula $$(N=P)_n Cl_m R^1_p \quad \text{(I)}$$

with, a hydroxy aryl compound represented by the general formula $$HOAr \quad \text{(II)}$$

where
$R^1$ represents hydroxy group, $NH_2$ group, $-OR^4$ group, $-SR^4$ group or

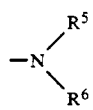

group, where $R^4$, $R^5$ and $R^6$ represent independently an alkyl group, an alkenyl group, alkynyl group or an aryl group or one of $R^5$ or $R^6$ may be hydrogen or $R^5$ and $R^6$ may form, together with a nitrogen atom bonded thereto, a saturated or an unsaturated heterocyclic ring,
n is an integer of 3 to 20,
m is an integer of 1 to 2n,
p is 2n−m,
Ar represents substituted or unsubstituted phenyl, substituted or unsubstituted naphthyl, or substituted or unsubstituted N-maleimidophenyl,
l is an integer of 1 to m, wherein the reaction is carried out under the presence of an acid acceptor and a pyridine derivative represented by the formula

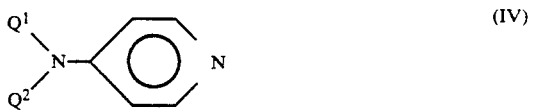

where $Q^1$ and $Q^2$ represent identical or different lower alkyl groups or constitute together with a nitrogen atom bonded thereto, a pyrrolidine ring, piperidine ring or morpholine ring.

17 Claims, No Drawings

PROCESS FOR PRODUCING ARYLOXY-SUBSTITUTED PHOSPHAZENE DERIVATIVES

This application is a continuation of application Ser. No. 07/157,321 filed Feb. 18, 1988, now abandoned.

BACKGROUND OF THE INVENTION

1. Field of the Invention

The present invention concerns a process for producing aryloxy-substituted phosphazene derivatives, for which industrial application use has now been developed, such as flame retardants, lubricating oils, electric insulators, hydraulic oils or starting materials therefor.

2. Description of the Prior Art

For oxyphosphazene derivatives obtained by alkoxylation and/or aryloxylation of chlorophosphazene oligomers having cyclic or chain structure

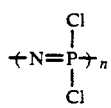

where n is an integer of 3 or greater, particularly, a cyclic chlorophosphazene oligomer

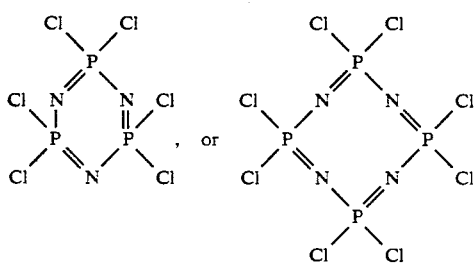

where n is 3 or 4, or chlorophosphazene oligomer mixtures comprising them as the main ingredient, or polymeric compounds resulted from their condensation, application uses as various industrial materials have now been developed owing to their excellent heat resistance, chemical resistance, lubricity, electric insulation property or chemical stability.

Various methods used for producing these materials, i.e., substitution of chlorine atoms bonded to phosphorus atoms in the phosphazene skelton (hereinafter referred to as "active chlorine atoms") with an aryloxy groups represented by the formula

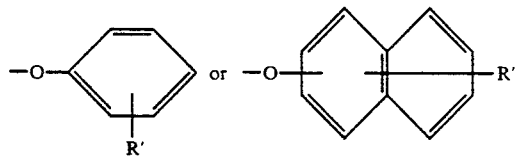

(where R' represents hydrogen or a substituent other than after mentioned maleimido group, for instance, an alkyl group, an alkoxy group or a halogen atom) as illustrated in "Phosphorus-Nitrogen Compounds", pp. 150-155, written by H. R. Allcock, published by Academic Press Inc. (1972). Then, the known methods of substituting active chlorine atoms with aryloxy groups (phenoxy group, for instance) may generally be classified into methods of reacting active chlorine atoms, with:

(1) phenol in the form of an alkali metal salt, (2) phenol as it is, using a hydroxide or carbonate of alkali metal as an acid acceptor, (3) phenol while using a tertiary amine as an acid acceptor, and (4) phenol under the presence of an acid acceptor using a phase transfer catalyst (U.S. Pat. No. 4,600,791, July 15, 1981).

Further, the production process wherein the aryloxy group is a 4-maleimidophenoxy group represented by the formula

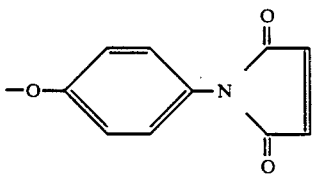

is described in U.S. Pat. No. 4,550,177 or "Journal of Polymer Science", Polymer Chemistry Edition, vol. 22, pp. 927-943 (1984), etc.

However, the method (1) described above takes an extremely long period of time to completely replace the all active chlorine atoms with the aryloxy groups.

In the method (2) described above, a side reaction is liable to occur, in which by-produced water reacts with the active chlorine atoms or with substituted oxy groups already bonded to the phosphorus atoms in the phosphazene skelton to cause P—OH bonding.

In the method (3) described above, it is generally difficult to completely replace the active chlorine atoms entirely with the phenoxy groups, although there is an exception such as the case of p-nitrophenol.

Then, the method (4) described above requires an expensive catalyst in a considerably great amount and a relatively long time for the completion of the reaction. Further, since water is used in this reaction, there is a great possibility that by-products having —OH groups are resulted in the case of using easily hydrolyzable material (for example, linear chlorophosphazene oligomer) as the starting material.

Further, since all of the reactions from (1) to (4) are conducted under heating, in the case where a phosphazene oligomer, which has substituents easily polymerizable by heating (for example, an aliphatic group having unsaturated bonding), is used as the starting material, it is inevitable to form by-products by polymerization. Furthermore, in these reactions, it is difficult to control the substitution of the active chlorine atoms with the aryloxy group to desired step.

While on the other hand, in a case where the aryloxy group is a 4-maleimidophenoxy group represented by

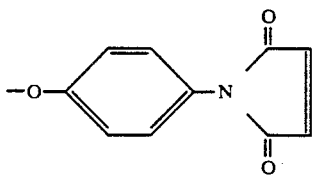

4-maleimidophenol is not directly reacted in the method of the literature described above but in extremely complicated procedures including a plurality of steps such as reaction of hexachlorocyclotriphosphazene (hereinafter simply referred as "3PNC") with 4-nitrophenolate or with 4-nitrophenolate and phenolate, followed by hydrogen reduction of the nitro group under pressure, maleamidation of the resultant amino group and formation of the aimed product by the dehydrating ring closing. Further by this method, the final yield is low, and it can not be acceptable from the economical point of view.

Further, the present inventors have previously offered a method of reacting 4-maleimidophenol directly with a chlorophosphazene oligomer in order to overcome the foregoing drawback (U.S. patent application Ser. No. 090,368), but it requires still a long period of time for the completion of the reaction.

SUMMARY OF THE INVENTION

The present inventors have found that the substituting reaction of chlorine atoms bonded to phosphorus atoms in a chlorophosphazene derivative with aryloxy groups under the presence of an acid acceptor can be proceeded easily and completely, or the number of substituents can optionally be controlled as required, while suppressing the side reaction as low as possible, when a kind of pyridine derivatives is used as a catalyst, and have accomplished the present invention based on these findings.

The present invention concerns a process for producing an aryloxy-substituted phosphazene derivative represented by the formula (III) shown later, which comprises of reacting a chlorophosphazene derivative represented by the general formula $$(N=P)_n Cl_m R^1_p \qquad (I)$$

where $R^1$ represents hydroxy group, $NH_2$ group, $-OR^4$ group, $-SR^4$ group or

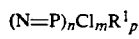

group, where $R^4$, $R^5$ and $R^6$ represent independently an alkyl group, an alkenyl group, alkynyl group or an aryl group or one of $R^5$ or $R^6$ may be hydrogen or $R^5$ and $R^6$ may form, together with a nitrogen atom bonded thereto, a saturated or an unsaturated heterocyclic ring, n is an integer of 3 or greater, m is an integer of 1 to 2n, p is 2n−m and, if p is 2 or greater, all of $R^1$ may be identical, or all or a portion of $R^1$ may be different each other, solely or as a mixture, with a hydroxy aryl compound represented by the general formula HOAr  (II)

where

Ar represents

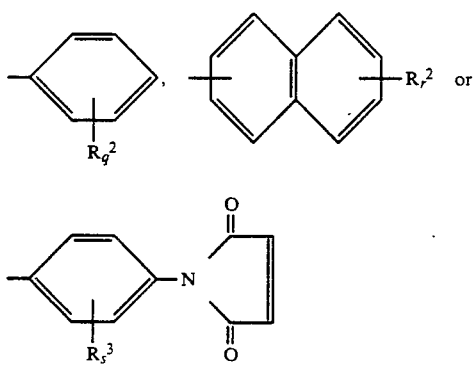

$R^2$ represents a halogen atom, cyano group, nitro group, alkyl group, haloalkyl group, alkoxy group, haloalkoxy group, alkyl carbonyl group, alkoxy carbonyl group, haloalkyl carbonyl group, haloalkoxy carbonyl group, di-substituted amino group, pyrrolidino group which may contain alkyl group, piperidino group which may contain alkyl group, morpholino group, cycloalkyl group, aryl group, aryloxy group, arylcarbonyl group or acid amide group;

$R^3$ represents a halogen atom, lower alkyl group, lower alkoxy group or lower alkoxy lower alkyl group, and q is an integer of 0 to 5, r is an integer of 0 to 7, s is an integer of 0 to 4, thereby producting an aryloxy-substituted phosphazene derivative represented by the general formula $$(N=P)_n(OAr)_l Cl_{m-l} R^1_p \qquad (III)$$

where Ar, $R^1$, n, m and p have the same meanings as described above, l is an integer of 1 to m, in which OAr by the number of l may be identical or different with each other when l is a plural number, wherein the reaction is carried out under the presence of an acid acceptor and a pyridine derivative represented by the formula

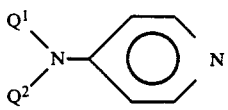

where $Q^1$ and $Q^2$ represent identical or different lower alkyl groups or constitute together with a nitrogen atom bonded thereto a pyrrolidine ring, piperidine ring or morpholine ring as a catalyst.

The process according to the present invention is advantageously carried out in an inert organic solvent.

Explanation will be made for the details of the process according to the present invention.

PHOSPHAZENE DERIVATIVE

As a dichlorophosphazene oligomer in the chlorophosphazene derivatives represented by the general formula (I) wherein m=2n, that is, p=0, a mixture of various oligomers represented by the formula

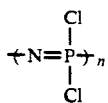

obtained by the reaction of phosphorus pentachloride and ammonium chloride may be used as it is. Alternatively, it is also possible to use a cyclic trimer (3PNC) or cyclic tetramer (4PNC) isolated and purified from the mixture individually or as an appropriate mixture thereof. They may be a starting material for the chlorophosphazene derivative of the general formula (I) where $p \geq 1$.

Among the groups represented by $R^1$ in the chlorophosphazene derivatives represented by the general formula (I), an alkyl group, an alkenyl group and an alkynyl group of $-OR^4$, $SR^4$ and

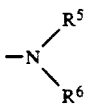

may have a substituent such as a halogen atom, a cyano group, a nitro group, an alkoxy group, a haloalkoxy group, an alkoxycarbonyl group, a haloalkoxycarbonyl group, a di-substituted amino group (two substituents and a nitrogen atom may form a ring which may further be substituted), a cycloalkyl group, an aryl group, an aryloxy group, a saturated heterocyclic group or a unsaturated heterocyclic group. When the formula

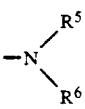

represents a heterocyclic ring, the ring may have a substituenet such as an alkyl group, and the ring may contain further a hetero atom.

An aryl group of $-OR^4$, $SR^4$ and

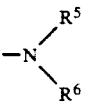

may have a substituent such as a halogen atom, a cyano group, a nitro group, an alkyl group, a haloalkyl group, an alkoxy group, a haloalkoxyl group, an alkyl carbonyl group, an alkoxy carbonyl group, a haloalkyl carbonyl group, a haloalkoxy carbonyl group, a di-substituted amino group, a pyrrolidino group which may have an alkyl group, a piperidino group which may have an alkyl group, a morpholino group, a cycloalkyl group, an aryl group, an aryloxy group, an aryl carbonyl group, an acid amide group or an acid imide group.

Further, either one of $R^5$ and $R^6$ may represent a hydrogen atom.

HYDROXY ARYL COMPOUND

In the hydroxy aryl compound represented by the general formula (II), when $R^2$ represents an alkyl group, a haloalkyl group, an alkoxy group or a haloalkoxy group, $R^2$ preferably has from 1 to 10 carbon atoms; when $R^2$ represents an alkyl carbonyl group, a haloalkyl carbonyl group, an alkoxy carbonyl group or a haloalk- oxy carbonyl group, the alkyl, haloalkyl, alkoxy or haloalkoxy moiety thereof preferably has from 1 to 10 carbon atoms, and when $R^2$ represents a di-substituted amino group, substituents may be alkyl groups and/or aryl groups.

$R^3$ preferably has from 1 to 5 carbon atoms in a case where it is a lower alkyl group or a lower alkoxy group, and preferably has from 1 to 5 carbon atoms for each of the lower alkoxy and lower alkyl moieties, in a case if it represents a lower alkoxy lower alkyl group.

Typical examples of the hydroxy aryl compound represented by the general formula (II) are shown below with no particular restrictions only thereto.

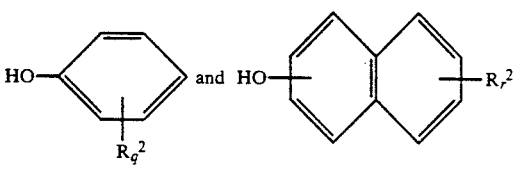

can include phenol, α-naphthol, β-naphthol, as well as the following compounds:

In a case where $R^2$ is an alkyl group, for example: o-cresol, m-cresol, p-cresol, o-ethylphenol, m-ethylphenol, p-ethylphenol, p-sec-butylphenol, p-tertoctylphenol, 2-methyl-α-naphthol, 4-methyl-α-naphthol, 3,4-dimethylphenol, 2,6-dimethylphenol.

In a case where $R^2$ is an alkoxy group for example: o-methoxyphenol, m-methoxyphenol, p-methoxyphenol, 4-methoxy-α-naphthol.

In a case where $R^2$ is a halogen atom, for example, o-chlorophenol, m-chlorophenol, p-chlorophenol, o-bromophenol, m-bromophenol, p-bromophenol, 2-chloro-α-naphthol, 4-chloro-α-naphthol, 1-bromo-β-naphthol, 6-bromo-β-naphthol, 2,3,4,5,6-pentachlorophenol, 3,4,5,6-tetrabromophenol, 2,3,4,5,6-pentabromophenol.

In a case where $R^2$ is a nitro group, for example: o-nitrophenol, m-nitrophenol, p-nitrophenol, 2-nitro--naphthol, 4-nitro-α-naphthol.

In a case where $R^2$ is a haloalkyl or haloalkoxy group, for example: o-trifluoromethylphenol, m-trifluoromethylphenol, p-trifluoromethylphenol, o-trifluoromethoxyphenol, m-trifluoromethoxyphenol, p-trifluoromethoxyphenol.

In addition, there may be also mentioned, for example: o-acetylphenol, m-acetylphenol, p-acetylphenol, p-ethylcarbonylphenol, o-(N,N,-dimethylamino)-phenol, m-(N,N,-dimethylamino)phenol, p-(N,N,-dimethylamino)phenol, p-methoxycarbonylphenol, p-acetoamidophenol, p-phenylphenol, p-phenoxyphenol, p-phenylcarbonylphenol, 2-methoxy-4-methyl-phenol, 2-methyl-4-chlorophenol, etc.

The compound represented by the formula

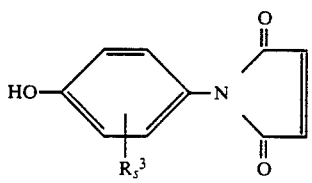

can include N-(4-hydroxyphenyl)maleimide, as well as the following compounds.

In a case where R³ is an alkyl group, for example: N-(2-methyl-4-hydroxyphenyl)maleimide, N-(2-ethyl-4-hydroxyphenyl)maleimide, N-(2-propyl-4-hydroxyphenyl)maleimide, N-(2-butyl-4-hydroxyphenyl)maleimide, N-(2,6-dimethyl-4-hydroxyphenyl)maleimide, N-(3,5-dimethyl-4-hydoxyphenyl)maleimide, N-(3,6-dimethyl-4-hydroxyphenyl)maleimide, N-(2,6-diethyl-4-hydroxyphenyl)maleimide, N-(2-methyl-3-ethyl-4-hydroxyphenyl)maleimide.

In a case where R³ is a lower alkoxy group, for example: N-(2-methoxy-4-hydroxyphenyl)maleimide, N-(2-ethoxy-4-hydroxyphenyl)maleimide, N-(2-propoxy-4-hydroxyphenyl)maleimide, N-(2-butoxy-4-hydroxyphenyl)maleimide, etc.

In a case where R³ is a halogen atom, for example: N-(2-chloro-4-hydroxyphenyl)maleimide, N-(2,6-dichloro-4-hydroxyphenyl)maleimide, N-(2-bromo-4-hydroxyphenyl)maleimide, N-(2,6-dibromo-4-hydroxyphenyl)maleimide, etc.

Further, there may also be mentioned, for example: N-(2-methoxyethyl-4-hydroxyphenyl)maleimide, N-(2-methyl-3-methoxy-4-hydroxyphenyl)maleimide, N-(2-ethoxy-3-ethyl-4-hydroxyphenyl)maleimide, N-(2-propoxy-3-methyl-4-hydroxyphenyl)maleimide, N-(2-butoxy-6-methyl-4-hydroxyphenyl)maleimide, etc.

These hydroxy aryl compounds may be used alone or combined, and they may be used in an equimolar amount to active chlorine atoms in the phosphazene derivative to be substituted. Of course they may be used in a slight excess than the equimolar amount in a case where all of the active chlorine atoms are to be substituted. In this specification, as the quotient obtained by dividing the molecular weight of a hydroxy aryl compound with the number of hydroxy groups contained in the hydroxy aryl compound is defined as one equimolar amount of the hydroxy aryl compound.

CATALYST

For the pyridine derivative represented by the general formula (III) as the catalyst in the present invention, 4-dimethylaminopyridine, 4-diethylaminopyridine, 4-pyrrolidinopyridine or 4-piperidinopyridine, etc. are suitable.

Referring to the amount of the catalyst used, although the catalyst effect can be obtained even from a small amount such as 1/200 mol based on one mol of the active chlorine atoms, somewhat longer reaction time is required when such an amount is used. It is usually appropriate to use the catalyst in an amount from about 1/30 mol to about 1/20 mol based on one mol of the active chlorine atoms, but the catalyst may be used in an amount of about 1/10 mol.

ACID ACCEPTOR

The inorganic strong base used in the present invention can include hydroxides of alkali metal and alkaline earth metal, carbonate of alkali metal, etc., and sodium hydroxide, potassium hydroxide, calcium hydroxide, sodium carbonate or potassium carbonate can also be used easily.

What is most interesting in the process according to the present invention is that the tertiary amine shows specificity when it is used as the acid acceptor, depending on the kind of the hydroxy aryl compounds employed.

That is, when the hydroxy compound represented by the general formula (II) is 4-maleimidophenol represented by the formula

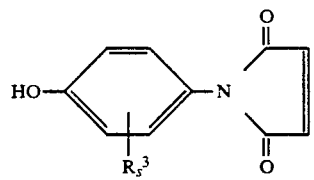

any optional tertiary amines may be used as the acid acceptor, whereas when the hydroxy aryl compound is represented by the formula

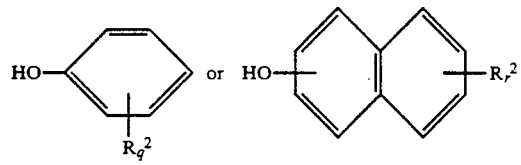

the reaction proceeds smoothly only in the case of using the tertiary amine represented by the general formula (V) and the active chlorine atoms in the starting phosphazene derivative can be substituted easily and completely. In the case of using other kinds of tertiary amines, for example, pyridine or N,N-dimethylaniline, the active chlorine atoms can not completely be substituted as shown later in Comparative Examples.

Tertiary amines of general formula V are represented by the formula

where
- X¹ represents an alkyl group, cycloalkyl group or aralkyl group, and
- X² and X³ represent identical or different lower alkyl groups or may constitute together with a nitrogen atom bonded thereto a pyrrolidine ring, piperidine ring or morpholine ring.

The tertiary amine represented by the general formula (V) can include, for example, methyldiethylamine, triethylamine, N,N-dimethylbutylamine, N,N-diethylbutylamine, N,N-dimethyloctylamine, N,N-diethyloctylamine, N,N-dimethyldodecylamine, N,N-dimethylstearylamine, N,N-dimethylcyclohexylamine, N,N-diethylcyclohexylamine, N-methylpyrrolidine, N-methylpiperidine, etc.

The tertiary amine, which is not represented by the formula (V) can include, for instance, N,N-dialkylaminophenyl derivatives such as, N,N-dimethylaniline, N,N-diethylaniline, N,N-dimethyltoluidines, pyridines such as pyridine or alkyl substituted pyridine, for example, α-picoline, β-picoline, α-picoline, 5-ethylpicoline, trimethylpyridine, etc.; quinolines such as quinoline, isoquinoline, alkyl-substituted quinoline or alkyl-substituted isoquinoline, for example, α-methylquinoline, β-methylquinoline, α-methylquinoline, 5-methylquinoline, etc. with no restrictions only thereto.

In a case where the hydroxy aryl compound represented by the general formula (II) is a 4-maleimidophenoxy compound, pyridines are particularly preferred as the tertiary amine for the acid acceptor.

The acid acceptor is used suitably in an equivalent or slightly excessive amount to the active chlorine atoms to be substituted.

REACTION MEDIUM

While the present invention can be carried out without using any organic solvent, it is advantageously conducted in an inert organic solvent for controlling the reaction temperature, reaction rate, etc.

The inert organic solvent is such an organic solvent as to not disturb the aryloxylating reaction for the skelton of a chlorophosphazene derivative as the starting material (which proceeds under the effect of the hydroxy aryl compound, the acid acceptor and the catalyst). Such solvent can include, for example, aromatic solvent such as benzene, toluene and monochlorobenzene; petroleum type solvent such as hexane, heptane, ligroin, petroleum ether; aprotic polar solvent such as dimethylformamide, acetonitrile and dimethylsulfoxide; ketone type solvent such as acetone and methyl ethyl ketone; ether type solvent such as ethyl ether, tetrahydrofuran and dioxane; ester type solvent such as ethyl formate and ethyl acetate; and chloroform, carbon tetrachloride and carbon disulfide.

In the reaction according to the present invention, the tertiary amine used as the acid acceptor corresponding to each of the hydroxyaryl compounds may be used in excess for serving also as the inert organic solvent.

Inert organic solvents usable in the present invention are of course not restricted only to the examples above.

Among the solvents exemplified above, those convenient are such solvents that are not miscible with water and do not dissolve salts formed by the reaction. In particular toluene, monochlorobenzene, etc. can be used conveniently.

The amount of the inert organic solvent used is preferably to such an amount as capable of dissolving the starting material and smoothly stirring the reaction system.

OPERATION METHOD

Most usual operations for conducting the reaction of the present invention will be explained below.

Inert organic solvent (for example, monochlorobenzene), hydroxy aryl compound, acid acceptor and catalyst are charged in a reaction vessel and, while stirring them, a solution of a chlorophosphazene derivative in an inert organic solvent is dropped thereto. In a case where the acid acceptor is an inorganic strong base, it is convenient to use the base as an aqueous solution, but it may be used also in a solid state, for example, flaky, granular or powdery form.

While the reaction temperature varies depending on the kind of the solvent used, the amount of the catalyst used, the reactivity of the starting materials to be used, etc. The reaction satisfactorily proceeds generally at a temperature within an approximate range of 0° C. to 60° C., in most cases, from about 10° C. to about 30° C.

While the reaction time also varies depending on the kind of acid acceptor, the kind of solvent, the amount of the catalyst used, the reactivity of the starting material and the reaction temperature, the reaction is completed in about 1 hour to about 24 hours.

In a case where the aimed aryloxy-substituted phosphazene derivative is a substance not containing active chlorine atoms, completion of the reaction can be checked by a pyridine-aniline mixture reagent. That is, a droplet of the reaction solution is placed on a filter paper or on a plate for thin layer chromatography and, after evaporating the solvent, a mixed solution of pyridine and aniline in 1:1 weight ratio is sprayed. If active chlorine atoms are present in the specimen, the spot of the specimen directly develops red color, and the color appears deeper as the amount of active chlorine atoms is greater.

In a case where the acid acceptor is a tertiary amine, hydrochloride of the acid acceptor deposited after the completion of the reaction is filtered off, the filtrate is washed with a small amount of an aqueous acid solution, aqueous alkaline solution and water successively, dried by adding a drying agent (for example, anhydrous sodium sulfate) and then the solvent is distilled of under a reduced pressure to obtain the aimed product as the residue.

Alternatively, the reaction solution may be washed with water to remove the hydrochloride instead of filtering off the same.

In a case where an aqueous solution of a strong inorganic base is used as the acid acceptor, the reaction solution is stood still after the completion of the reaction to separate an aqueous layer from an organic solvent layer, followed by the subsequent treatment in accordance with the above-mentioned procedures.

EXAMPLE 1

Into a one liter flask, 162.1 g (1.723 mol) of phenol, 261.1 g (2.583 mol, 1.5 times of the theoretical amount) of triethylamine and 11.2 g (0.092 mol) of 4-dimethylaminopyridine were charged and, while stirring, a solution of 100 g (0.287 mol) of hexachlorocyclotriphosphazene (hereinafter simply referred to as "3PNC") dissolved in 300 ml of monochlorobenzene was dropped over one hour. Since the reaction was exothermic, stirring was continued while cooling with water for 5 hours at a temperature of about 27° C. Deposited triethylamine hydrochloride was filtered off and the filtrate was washed with an aqueous hydrogen chloride solution, an aqueous sodium hydroxide solution and water successively and dried with anhydrous sodium sulfate. Then, monochlorobenzene was distilled off under the reduced pressure to obtain 195.5 g (98.3% yield) of hexakis(phenoxy)cyclotriphosphazene

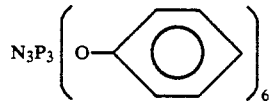

The substance was a white solid having a melting point of 114.5° to 115.5° C. (literatures value: 115°-115.5° C.). The results of gel permeation chromatography (hereinafter simply referred to as "GPC") and liquid chromatography (hereinafter simple referred to as "LC") analysis of the solid matter showed that the matter comprised a single substance, and the active chlorine atoms remaining therein was less than 0.01%.

EXAMPLE 2

The same experiment as in Example 1 was carried out excepting for using 133.2 g (0.287 mol) of octachlorocyclotetraphosphazene (hereinafter simply referred to as "4PNC") instead of 100 g of 3PNC used in Example 1, 216.1 g (2.296 mol) of phenol, 348.1 g (3.44 mol) of triethylamine and 14.96 g (0.123 mol) of 4-dimethylaminopyridine, to obtain 261.2 g (yield 98.5%) of octa(phenoxy)cyclotetraphosphazene.

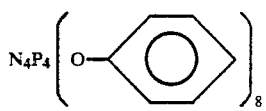

The substance was white solid having a melting point from 84.5° to 86.0° C. (literature value: 85.0°–86.0° C.).

The results of GPC analysis and LC analysis for the solid matter showed that the matter comprised a single substance, and the active chlorine atoms remaining therein was less than 0.01%.

EXAMPLE 3

The same experiment as in Example 1 was carried out excepting for using 100 g of a phosphonitrile chloride oligomer mixture (0.862 mol as 1 structural unit (N=PCl$_2$), the mixing ratio: 59.6% 3 PNC, 14.5% 4PNC and 29% other oligomers) instead of 3PNC used in Example 1 to obtain 189.3 g (95.3% yield) of white solid. The results of GPC analysis and LC analysis showed that the white solid was a mixture represented by the formula

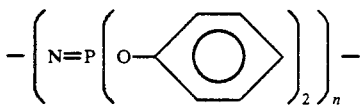

and the mixing ratio was substantially corresponded to that of the starting oligomer. The active chlorine atoms remaining in the mixture was less than 0.01%.

EXAMPLE 4

The same experiment as in Example 1 was carried out by using 13.6 g (0.092 mol) of 4-pyrrolidinopyridine instead of 4-dimethylaminopyridine used in Example 1 to obtain 194.3 g (97.7% yield) of hexakis(phenoxy)cyclotriphosphazene. The substance was white solid having a melting point of 114.7° to 115.0° C. The results of GPC analysis and LC analysis showed that the solid matter comprised a single substance. Further, the amount of the active chlorine atoms remaining therein was less than 0.01%.

EXAMPLE 5

The same experiment as in Example 1 was carried out excepting for using 328.6 g (2.583 mol) of N,N-dimethylcyclohexylamine instead of triethylamine used in Example 1 as an acid acceptor to obtain 194.9 g (98.0% yield) of hexakis(phenoxy)cyclotriphosphazene. The substance was white solid having a melting point of 114.0° to 115.0° C. The results of GPC analysis and LC analysis showed that the solid matter comprised a single substance. Further, the amount of the active chlorine atoms remaining therein was less than 0.01%.

EXAMPLE 6

The same experiment as in Example 1 was carried out excepting for using 255.7 g (2.583 mol) of N-methylpiperidine instead of triethylamine used in Example 1 as an acid accepter, to obtain 195.1 g (98.1% yield) of hexakis(phenoxy)cyclotriphosphazene. The substance was white solid having a melting point of 114° to 114.5° C. The results of GPC analysis and LC analysis showed that the solid matter comprised a single substance. Further, the amount of the active chlorine atoms remaining therein was less than 0.01%.

EXAMPLE 7

151.7 g (0.263 mol) of a cyclotriphosphazene compound represented by the formula $$N_3P_3(OCH_2CF_3)_{3.6}Cl_{2.4}$$

obtained from one mol of 3PNC and 3.6 mol of sodium alkoholate of trifluoroethanol was reacted with a mixture comprising 31.75 g (0.338 mol) of phenol, 25.4 g (0.235 mol) of m-cresol and 11.1 g (0.103 mol) of p-cresol in 300 ml of monochlorobenzene using 104.4 g (1.03 mol) of triethylamine as an acid acceptor and 4.49 g (0.037 mol) of 4-dimethylaminopyridine as a catalyst under the same conditions as in Example 1 to obtain 180.3 g of pale yellow oily substance. The results of GPC analysis, LC analysis and NMR spectral analysis showed that the oily substance was a mixture mainly composed of a cyclotriphosphazene compound having the structure

The amount of active chlorine remaining in the oily substance was less than 0.01%.

EXAMPLE 8

The same experiment as in Example 7 was carried out excepting for using 139.2 g (1.03 mol) of N,N-dimethylbenzylamine as an acid acceptor instead of triethylamine used in Example 7 to obtain 175.4 g of pale yellow oily substance. The results of GPC analysis, LC analysis and NMR spectral analysis showed that the oily substance was a cyclotriphosphazene compound having the structure

The amount of active chlorine remaining in the oily substance was less than 0.01%.

EXAMPLE 9

136.1 g (0.263 mol) of trichloro-tris(phenylamino)cyclotriphosphazene represented by the formula

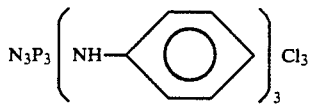

obtained from 1 mol of 3PNC and 3 mol of aniline was reacted with 81.6 g (0.82 mol, 1.1 times amount of the theoretical amount) of phenol in 300 ml of monochlorobenzene under the presence of 119 g (1.18 mol, 1.5 times of the theoretical amount) of triethylamine and 5.14 g (0.042 mol) of 4-dimethylaminopyridine under the same conditions as in Example 1 to obtain 185.2 g (93.5% yield) of white solid. The results of GPC analysis, LC analysis and NMR spectral analysis showed that the substance was a cyclotriphosphazene compound represented by the formula

The amount of active chlorine atoms remaining in the solid matter was less than 0.01%.

EXAMPLE 10

By decreasing the amount of 4-dimethylaminopyridine used as the catalyst in Example 1 to 1/10, that is to, 1.12 g and using other substances in the same amounts as those in Example 1, reaction was continued for 24 hours at a reaction temperature of 50° C. Subsequent procedures were carried out in the same manner as in Example 1 to obtain 194.5 g (97.8% yield) of hexakis(phenoxy)cyclotriphosphazene. The substance was white solid having a melting point of 115.0° to 115.5° C. The results of GPC analysis and LC analysis showed that the solid matter comprised a single substance and the amount of active chlorine atoms remaining therein was less than 0.01%.

EXAMPLE 11

Into a one liter flask, 103.4 g (2.583 mol) of sodium hydroxide and 200 ml of water were added and dissolved, to which 162.1 g (1.723 mol) of phenol and 11.2 g (0.092 mol) of 4-dimethylaminopyridine were charged and, while stirring, a solution of 100 g (0.287 mo.) of 3PNC dissolved in 300 ml of monochlorobenzene was dropped for one hour. Since the reaction was exothermic, stirring was continued at a temperature of about 27° C. for 8 hours while cooling with water. After the completion of the reaction, the reaction solution was stood still to separate an aqueous layer. The organic layer was then washed with an aqueous hydrogen chloride solution, an aqueous sodium hydrogen carbonate solution and water successively, and then dried with an addition of anhydrous sodium sulfate. Then, monochlorobenzene was distilled off under a reduced pressure to obtain 189.5 g (95.3% yield) of hexakis(phenoxy)cyclotriphosphazene. The substance was white solid having a melting point of 114.0° to 115.0° C. The results of GPC analysis and LC analysis showed that the solid matter comprised a single substance and the amount of active chlorine atoms remaining therein was less than 0.01%.

EXAMPLE 12

This experiment was conducted according to Example 11 using 336.4 g (2.583 mol) of anhydrous potassium carbonate instead of sodium hydroxide used in Example 11. Active chlorine atoms disappeared after 12 hours. By applying the same subsequent procedures as in Example 11, 188.7 g (94.9% yield) of hexakis(phenoxy)cyclotriphosphazene was obtained. The substance was white solid having a melting point of 114.2° to 115.0° C. The results of GPC analysis and LC analysis showed that the solid matter comprised a single substance and the amount of active chlorine atoms remaining therein was less than 0.01%.

EXAMPLE 13

The same experiment as in Example 1 was carried out excepting for changing the amount of phenol, 4-dimethylaminopyridine and triethylamine used in Example 1 to 81.0 g (0.862 mol), to 5.6 g (0.046 mol) and to 130.8 g (1.29 mol) respectively, to obtain 145.2 g (yield 97.2%) of viscous pale yellow liquid.

The analysis value for the active chlorine atoms remaining in the viscous liquid was 20.1%. The theoretical amount of Cl in

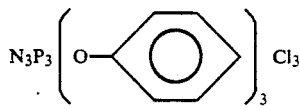

was 20.43%. The result of LC analysis (simple area %) showed that the viscous liquid was a mixture having the following composition comprising

 92.0%,

 6.1%, and

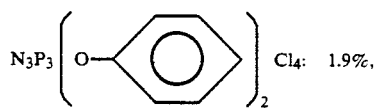 1.9%,

EXAMPLE 14

The same experiment as in Example 1 was carried out excepting for using 14.9 g of 4-piperidinopyridine instead of 4-dimethylaminopyridine used in Example 1 to obtain substantially the same result as in Example 1.

EXAMPLE 15

The same experiment as in Example 1 was carried out excepting for using 219.7 g (2.583 mol) of N-methylpyrrolidine instead of triethylamine used in Example 1 to obtain substantially the same result as in Example 1.

EXAMPLE 16

Into a one liter flask, 81.05 g (0.862 mol) of phenol, 384.3 g (1.292 mol, 1.5 times of the theoretical amount) of N,N-dimethylstearylamine, 5.6 g (0.046 mol) of 4-dimethylaminopyridine and 300 ml of monochlorobenzene were charged and, while stirring, a solution of 50 g of 3PNC dissolved in 150 ml of monochlorobenzene was dropped for one hour. After the completion of dropping they were reacted by heating for 24 hours while maintaining the internal temperature at 50° C. The procedures after the completion of the reaction were the same as those in Example 1, to obtain 97.0 g (92.6% yield) of hexakis(phenoxy)cyclotriphosphazene.

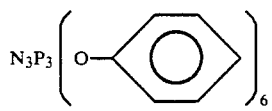

The amount of active chlorine atoms remaining therein was less than 0.01%.

EXAMPLE 17

The same experiment as in Example 16 was carried out excepting for using 130.5 g (1.292 mol) of N,N-dimethyl-n-butylamine instead of N,N-dimethylstearylamine used in Example 16 to obtain substantially the same results as in Example 16.

EXAMPLE 18

15.0 g (0.018 mol, chlorine content 0.056 mol) of a mixture of cyclotriphosphazene partially substituted with maleimidophenoxy group and mainly composed of substance represented by the formula

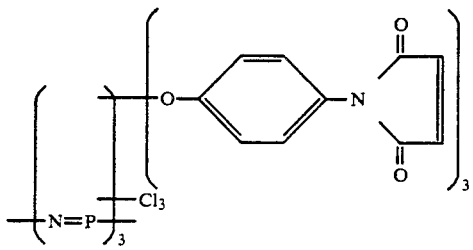

obtained by the reaction of 3PNC and N-(4-hydroxylphenyl)maleimide was reacted with 5.26 g (0.056 mol) of phenol, 8.50 g (0.084 mol) of triethylamine and 0.34 g (0.0028 mol) of 4-dimethylaminopyridine in 200 ml of tetrahydrofuran under substantially the same conditions as in Example 1 to obtain 17.9 g of pale brown resinous solids. As the results of NMR spectral analysis and LC analysis, it was found that the substance of the pale brown resinous solids was a mixture mainly composed of cyclotriphosphazene represented by the formula

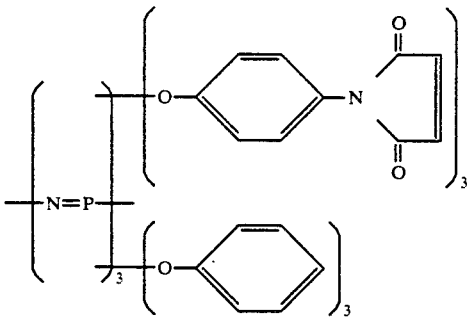

The amount of active chlorine atoms in the resinous solid substance was less than 0.01%.

COMPARATIVE EXAMPLE 1

Reaction was carried out in the same manner as in Example 1 for 5 hours at a temperature of about 27° C. by using 204.3 g (2.583 mol) of pyridine instead of triethylamine used as the acid acceptor in Example 1. When a small amount of the reaction solution was sampled and detected for remaining active chlorine atoms by a pyridine-aniline mixture reagent, it showed a deep red color indicating that a great amount of active chlorine atoms remained. After elevating the reaction temperature to 60° C. and further continued stirring for 48 hours, the active chlorine atoms were detected in the same manner as above, but no substantial change was shown in the density of red color. The reaction product was applied with the same subsequent treatment in Example 1 to obtain 100 g of resinous substance. 12.3% of active chlorine atoms remained in the substance.

COMPARATIVE EXAMPLE 2

The same experiment as in Comparative Example 1 was carried out by using 309.9 g (2.583 mol) of N,N-dimethylaniline instead of pyridine in Comparative Example 1. Also in this case, a great amount of active chlorine atoms were still detected even after continuing the reaction at 60° C. for 48 hours in the same manner as in Comparative Example 1. Subsequent treatments were applied in the same manner as in Example 1 to obtain 89.5 g of resinous substance. 16.2% of active chlorine atoms remained in the substance.

COMPARATIVE EXAMPLE 3

After carrying out the reaction for 5 hours at a temperature of about 27° C. in the same manner as in Example 1 excepting for not using 4-dimethylaminopyridine used in Example 1, a great amount of active chlorine atoms were still detected.

COMPARATIVE EXAMPLE 4

After carrying out the reaction for 8 hours at a temperature of about 27° C. in the same manner as in Example 11 excepting for not using 4-dimethylaminopyridine used in Example 11, a great amount of active chlorine atoms were still detected.

COMPARATIVE EXAMPLE 5

100 g (0.287 mol) of 3PNC and 99.9 g (0.861 mol) of sodium phenolate were added to 300 ml of toluene and continuously stirred at a temperature of 50° C. for 8 hours. The solution was cooled and sodium chloride was filtered off. The filtrate was washed with an aqueous hydrogen chloride solution, an aqueous sodium carbonate solution and then with water successively, and after drying with anhydrous sodium sulfate, toluene was distilled off under a reduced pressure to obtain 140.3 g (93.9% yield) of viscous pale yellow liquid. The result of LC analysis (simple area %) showed that the viscous liquid was a mixture comprising

 $Cl_4$: 12.2%,

 $Cl_3$: 71.6%,

 $Cl_2$: 15.8% and

 $Cl$: 0.3%,

COMPARATIVE EXAMPLE 6

The same experiment as in Example 16 was carried out excepting for not using 4-dimethylaminopyridine, deep red color was still appeared in the pyridine-aniline mixture reagent test even after 35 hours from the start of the reaction, indicating that a great amount of active chlorine atoms remained.

COMPARATIVE EXAMPLE 7

In the Experiment carried out while removing 4-dimethylaminopyridine in Example 17, a great amount of active chlorine atoms were still present even 35 hours after the start of the reaction.

EXAMPLE 19

7.0 g (0.12 mol chlorine content) of a chlorophosphazene oligomer mixture comprising 58.7% 3PNC, 14.5% 4PNC and 26.3% of other chlorophosphazene oligomers was dissolved in 50 ml of tetrahydrofuran.

Into a 500 ml four-necked flask having a stirrer, a thermometer, a reflux condenser and a dropping funnel, 22.7 g (0.12 mol) of N-(4-hydroxyphenyl)maleimide, 14.3 g (0.18 mol) of pyridine, 0.74 g (0.006 mol) of 4-dimethylaminopyridine and 200 ml of tetrahydrofuran were charged and, while stirring, the above-mentioned solution of chlorophosphazene oligomer mixture was dropped for 30 minutes. The reaction was exothermic and, while the maximum temperature was elevated to 55° C., the reaction was continued as it was for 5 hours without cooling procedure. After the reaction was over, hydrochloride of pyridine was filtered out. About 150 ml of the solvent was distilled off from the filtrate under a reduced pressure and, the resultant liquid concentrate was added to 200 ml of ice-water to deposit viscous brown black resinous product. The aqueous layer was removed by decantation and the residual resinous product was dissolved in 50 ml of tetrahydrofuran and then the solution was again poured into 200 ml of ice-water to obtain a viscous brown resinous product.

After drying under a reduced pressure, 24.2 g of viscous brown resinous product was obtained, which was estimated as the results of IR spectral analysis and GPC analysis to be a substance represented by the formula

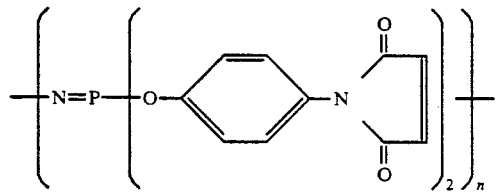

The content of active chlorine atoms was less than 0.01%.

EXAMPLE 20

7.0 g (0.12 mol chlorine content) of 3PNC was dissolved in 50 ml of tetrahydrofuran.

Into a 500 ml four-necked flask having a stirrer, a thermometer, a reflux condenser and a dropping funnel, 22.7 g (0.12 mol) of N-(4-hydroxyphenyl)maleimide, 14.3 g (0.18 mol) of pyridine, 0.73 g (0.006 mol) of 4-dimethylaminopyridine and 200 ml of tetrahydrofuran were charged and, while stirring, the above-mentioned solution of 3PNC was dropped for 30 minutes. The reaction was exothermic and, while the maximum temperature was elevated to 45° C., the reaction was continued as it was for 7 hours without cooling procedure. After the reaction was over, hydrochloride of pyridine was filtered out. About 150 ml of the solvent was distilled off from the filtrate under a reduced pressure and the resultant liquid concentrate was poured into 200 ml of ice-water to deposit viscous brown black resinous product.

The aqueous layer was removed by decantation and the residual resinous product was dissolved in 50 ml of tetrahydrofuran and then the solution was again poured into 200 ml of ice-water to obtain a viscous pale brown resinous product. After drying under a reduced pressure, 24.6 g of a viscous pale brown resinous product was obtained. The melting point of the product was 259°-262.5° C. It was confirmed by the GPC analysis and LC analysis that the product comprised a single substance and by the IR spectral analysis that is was 2,2,4,4,6,6-hexakis(maleimidophenoxy)cyclotriphosphazene represented by the formula

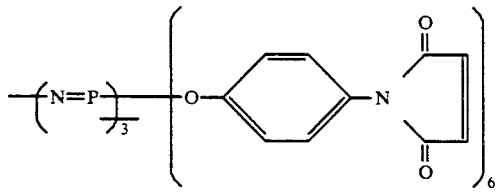

The content of active chlorine atoms was less than 0.01%.

EXAMPLE 21

After charging 7.0 g (0.12 mol of chlorine content) of 3PNC, 200 ml of tetrahydrofuran, 4.75 g (0.06 mol) of pyridine and 0.37 g (0.003 mol) of 4-dimethylaminopyridine in a one liter four-necked flask provided with a stirrer, a thermometer, a reflux condenser and a dropping funnel, a solution of 11.3 g (0.06 mol) of N-(4-hydroxyphenyl)maleimide dissolved in 50 ml of tetrahydrofuran was dropped over 30 minutes under stirring. The reaction was exothermic and while the maximum temperature was elevated to 55° C., the reaction was conducted as it was for 2 hours under the room temperature with no particular cooling. Then, the reaction solution was filtered to remove hydrochloride of pyridine and the solvent was distilled off from the filtrate to obtain 16.0 g of a brown resinous product. From the results of the quantitative determination for the active chlorine atoms, as the results of IR spectral analysis and LC analysis it was found that the resinous brown product was a mixture of partially substituted cyclotriphosphazenes with a maleimidophenoxy group mainly composed of substance represented by the formula

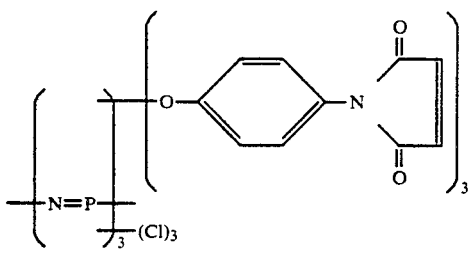

EXAMPLE 22

10.8 g (0.02 mol, chlorine content 0.06 mol) of a mixture of with a trifluoroethoxy group partially substituted cyclotriphosphazene compounds mainly composed of a substance represented by the formula

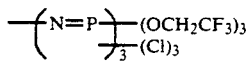

obtained from 1 mol of 3PNC and 3 mol of sodium alcoholate of fluoroethanol was charged together with 11.4 g (0.06 mol) of N-(4-hydroxyphenyl)maleimide, 7.15 g (0.09 mol) of pyridine, 0.37 g (0.003 mol) of 4-dimethylaminopyridine and 200 ml of tetrahydrofuran into a 500 ml three-necked flask equipped with a stirrer, a thermometer, and a reflux condenser. After stirring for 5 hours at a temperature of 27° C. the substantially same subsequent treatments as in Example 19 were conducted to obtain 18.2 g of a pale brown solid matter. As the results of IR spectral analysis, NMR analysis and LC analysis, the viscous resinous product was a mixture mainly composed of a substance represented by the formula

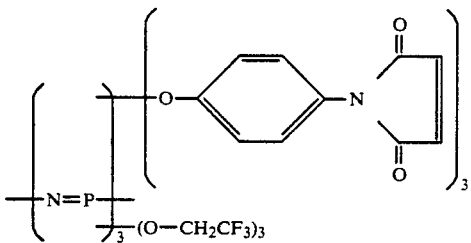

The content of active chlorine atoms in the resinous product was less than 0.01%.

EXAMPLE 23

7.0 g (0.12 mol chlorine content) of a 3PNC mixture was dissolved in 50 ml of monochlorobenzene.

Into a 500 ml four-necked flask having a stirrer, a thermometer, a reflux condenser and a dropping funnel, 11.4 g (0.06 mol) of N-4-(hydroxyphenyl)maleimide, 5.6 g (0.06 mol) of phenol, 18.2 g (0.18 mol) of triethylamine, 0.89 g (0.006 mol) of 4-pyrrodinopyridine and 200 ml of monochlorobenzene were charged and, while stirring, the above-mentioned monochlorobenzene solution of 3PNC was dropped for 20 minutes. The reaction was exothermic and, while the maximum temperature was elevated to 35° C., the reaction was continued as it was for 8 hours without cooling procedures. After the reaction was over, deposited hydrochloride of triethylamine was filtered out. The filtrate was washed with an aqueous hydrogen chloride solution, an aqueous sodium hydroxide solution and then with water successively and, after dried with anhydrous sodium sulfate, monochlorobenzene was the distilled off under a reduced pressure to obtain 19.3 g of pale brown resinous solid substance. As the results of IR spectral analysis and LC analysis, it was found that the resinous solid substance was a mixture mainly composed of

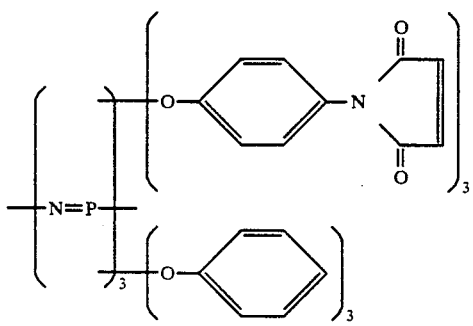

Further, the content of active chlorine atoms was less than 0.01%.

EFFECTS OF THE INVENTION

According to the present invention, upon producing an aryloxy-substituted phosphazene derivative represented by the general formula (III) by substituting chlorine atoms bonded to phosphorus atoms in a chlorophosphazene derivative with aryloxy groups, the reaction can be proceeded easily and completely, or the number of substituent groups in the product can optionally be controlled as required by incorporating a pyridine derivative represented by the general formula (IV) as a catalyst in the reaction system and combining an acid acceptor.

That is, each of the examples in the present invention discloses that the aimed product (that is, aryloxy-substituted phosphazene derivative represented by the general formula (III) can be produced at high purity and high yield while suppressing side reactions such as hydrolysis, polymerization or condensation as low as possible. Further, as apparent from the comparison between Example 13 and Comparative Example 5, tri-chlorotriphenoxyphosphazene in which ½ mol of active chlorine atoms of 3PNC is substituted with phenoxy groups can be obtained at 92% purity by using the catalyst according to the present invention. This shows that the number of the substituent groups can be controlled to desired steps.

What is claimed is:

1. A process for obtaining a substituted phosphazene, comprising reacting a chlorophosphazene of the formula $$(N=P)_n Cl_m R^1_p \tag{I}$$

or a mixture thereof, wherein $R^1$ is the same or different and is selected from the group consisting of $-NH_2$, $-OR^4$, $-SR^4$ and $-NR^5R^6$ where $R^4$, $R^5$ and $R^6$ represent independently alkyl unsubstituted or monosubstituted by halogen, cyano, nitro, alkoxy, haloalkoxy, alkoxycarbonyl, haloalkoxycarbonyl, cycloalkyl, carbocyclicaryl and carbocyclicaryloxy or carbocyclicaryl unsubstituted or monosubstituted by halogen, cyano, nitro, alkyl, haloalkyl, alkoxy, haloalkoxy, alkylcarbonyl, alkoxycarbonyl, haloalkylcarbonyl, haloalkoxycarbonyl, cycloalkyl, carbocyclicaryl, carbocyclicaryloxy, and carbocyclicarylcarbonyl, n is an integer of 3 to 20, m is an integer of 1 to 2n, p is an integer of (2n−m), with a compound of the formula

HOAr     (II)

wherein Ar is selected from the group consisting of

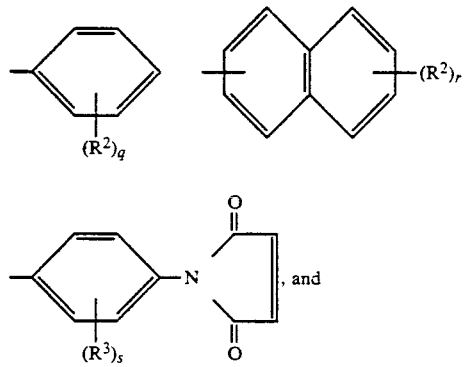

$R^2$ is selected from the group consisting of halogen, cyano, alkyl, haloalkyl, alkoxy, haloalkoxy, alkylcarbonyl, alkoxycarbonyl, haloalkylcarbonyl, haloalkoxycarbonyl, cycloalkyl, carbocyclicaryl, carbocyclicaryloxy, and carbocyclicarylcarbonyl, $R^3$ is selected from the group consisting of halogen, lower alkyl, lower alkoxy and lower alkoxy lower alkyl, q is an integer of 0 to 5, r is an integer of 0 to 7, and s is an integer of 0 to 4, at a temperature of about 0° to 60° C. in the presence of an acid acceptor and a catalyst comprising a pyridine derivative of the formula

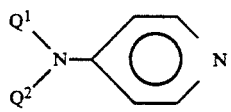

(IV)

wherein $Q^1$ and $Q^2$ represent identical or different lower alkyl or form, together with the nitrogen atom bonded thereto a pyrrolidine or piperidine ring, for a period of time effective to obtain a substituted phosphazene of the formula $(N=P)_n(OAr)_lCl_{m-l}R^1_p$     (III),

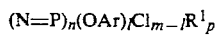

wherein Ar, $R^1$, n, m and p are as described above, l is an integer of 1 to m wherein when l is greater than 1 each OAr may be the same as or different from the others.

2. The process of claim 1, wherein the Ar group of the compound of formula (II) is

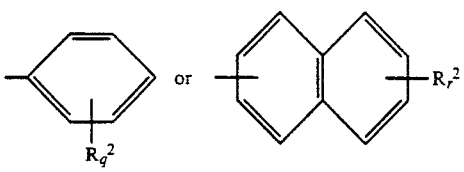

wherein $R^2$, q, and r are as described in claim 35; and the acid acceptor is at least one selected from the group consisting of strong inorganic bases and tertiary amines of the formula $(X^2X^3)N-X^1$     (V),

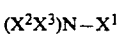

wherein $X^1$ is selected from the group consisting of alkyl, cycloalkyl and carbocyclicarylalkyl and $X^2$ and $X^3$ represent identical or different lower alkyl or constitute together with the nitrogen atom bonded thereto pyrrolidine, piperidine or morpholine.

3. The process of claim 2, wherein the Ar group of the compound of formula (II) is selected from the group consisting of

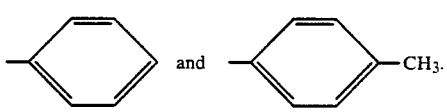

4. The process of claim 1, wherein
the catalyst of formula (IV) is selected from the group consisting of 4-dimethylaminopyridine, 4-pyrrolidinopyridine and 4-piperidinopyridine.

5. The process of claim 2, wherein
the acid acceptor is a tertiary amine of the formula (V), wherein
$X^1$ is selected from the group consisting of methyl, ethyl, butyl, cyclohexyl and stearyl; and
$X^2$ and $X^3$ are independently of one another methyl or ethyl, or together with the nitrogen atom bonded thereto form pyrrolidine or piperidine.

6. The process of claim 1, wherein the Ar group of the compound of formula (II) is

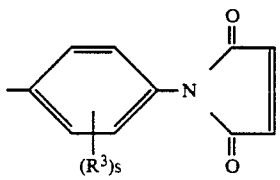

wherein $R^3$ and s are as described in claim 35 and the acid acceptor is at least one selected from the group consisting of strong inorganic bases,
N,N-dialkylaniline, N,N-dialkyltoluidine, pyridine, alkylsubstituted pyridine, quinoline, alkylsubstituted quinoline, isoquinoline or alkylsubstituted isoquinoline and tertiary amines of the formula $(X^2X^3)NX^1$     (V)

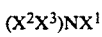

wherein $X^1$ is selected from the group consisting of alkyl, cycloalkyl and carbocyclicarylalkyl, and $X^2$ and $X^3$ represent identical or different lower alkyl.

7. The process of claim 6, wherein the catalyst of formula (IV) is selected from the group consisting of 4-dimethylaminopyridine, 4-pyrrolidinopyridine and 4-piperidinopyridine.

8. The process of claim 6, wherein
the acid acceptor is a tertiary amine of formula (V), wherein $X^1$ is selected from the group consisting of methyl, ethyl, butyl, cyclohexyl and stearyl, and $X^2$ and $X^3$ are independently methyl or ethyl.

9. The process of claim 1, wherein in the chlorophosphazene of formula (I)
$R^4$ is selected from the group consisting of phenyl and 4-methylphenyl, or
$R^5$ is phenyl and $R^6$ is hydrogen.

10. The process of claim 1, wherein in the chlorophosphazene of formula (I)
p is 0, n is 3 and m is 6;
p is 0, n is 4 and m is 8; or
p is 0, n is 3 to 20 and m is 2n.

11. The process of claim 6, wherein
in the chlorophosphazene of formula (I) $R^4$ is phenyl.

12. The process of claim 6, wherein in the chlorophosphazene of formula (I)
p is 0, n is 3 and m is 6;
p is 0, n is 4 and m is 8; or
p is 0, n is 3 to 20 and m is 2n.

13. The process of claim 1 wherein
the reaction is conducted in the presence of an inert organic solvent.

14. The process of claim 1, wherein
the reaction is conducted at a temperature of about 10° to 30° C.

15. The process of claim 1, wherein
the reaction is conducted for a period of time of about 1 to 24 hours.

16. The process of claim 1, wherein
the acid acceptor is present in an about equivalent amount with respect to the active chlorine atoms present in the chlorophosphazene of formula (I);
the catalyst is present in an amount of about 1:200 to 1:10 mol per mole of active chlorine atoms present in the chlorphosphazene of formula (I); and
the compound of formula (II) is present in an amount about equimolar or in excess of the amount of active chlorine atoms present in the chlorophosphazene of formula (I).

17. The process of claim 13, wherein
the inert solvent is selected from the group consisting of water-immiscible solvents and solvents that do not substantially dissolve salts formed by the reaction.

* * * * *